United States Patent [19]

Hsieh et al.

[11] 4,357,312

[45] Nov. 2, 1982

[54] METHOD OF MAKING PROLONGED RELEASE BODY

[75] Inventors: Dean S. T. Hsieh, Cambridge; Robert S. Langer, Jr., Somerville, both of Mass.

[73] Assignee: The Children's Hospital Medical Center, Boston, Mass.

[21] Appl. No.: 283,826

[22] Filed: Jul. 16, 1981

[51] Int. Cl.³ .................. A61K 9/22; A61K 9/26; A61K 31/74; A61K 31/78

[52] U.S. Cl. ............................. 424/15; 128/260; 264/28; 264/41; 264/49; 424/19; 424/22; 424/78; 424/81; 521/64

[58] Field of Search ............ 264/28, 41, 49; 521/64; 424/19-22, 15, 79-83; 128/260

[56] References Cited

U.S. PATENT DOCUMENTS

| | | | |
|---|---|---|---|
| 3,256,372 | 6/1966 | Adams et al. | 264/28 |
| 3,608,063 | 9/1971 | Banker | 424/22 |
| 3,629,392 | 12/1971 | Banker et al. | 424/22 |
| 3,756,967 | 9/1973 | Liebman et al. | 521/64 |
| 3,812,224 | 5/1974 | Smith et al. | 264/28 |
| 3,876,446 | 4/1975 | Bleckmann et al. | 264/28 |
| 4,118,449 | 10/1978 | Rinde | 264/28 |
| 4,134,943 | 1/1979 | Knitsch et al. | 264/28 |
| 4,164,560 | 8/1979 | Folkman et al. | 424/19 |
| 4,248,855 | 2/1981 | Blank et al. | 424/19 |
| 4,269,713 | 5/1981 | Yamashita et al. | 264/41 |

OTHER PUBLICATIONS

B. K. Davis, "Diffusion in Polymer Gel Implants", Proc. Nat. Acad. Sci. USA, vol. 7, No. 88, pp. 3120-3123.

*Primary Examiner*—Shep K. Rose

[57] ABSTRACT

In a method of making a biologically compatible, water-insoluble polymeric body for the controlled, prolonged release of a biologically active substance to a surrounding aqueous environment, the method including forming a liquid mixture containing the polymer, the active substance, and an organic solvent capable of dissolving the polymer, and solidifying the liquid mixture to form the polymeric body, the improvement wherein the liquid mixture further comprises water, the solidification is carried out by cooling the liquid mixture to a temperature sufficiently low to cause the water in the mixture to freeze, thereby creating channels in the body for the release of the active substance therefrom, and removing the organic solvent and the water from the body.

9 Claims, 2 Drawing Figures

METHOD OF MAKING PROLONGED RELEASE BODY

BACKGROUND OF THE INVENTION

This inventin relates to manufacturing biologically compatible, water-insoluble polymeric bodies for controlled, prolonged release of a biologically active substance to a surrounding aqueous environment.

Folkman et al, U.S. Pat. No. 4,164,560, hereby incorporated by reference, describes a method of making such a body by forming a liquid mixture containing the polymer, the active substance, and an organic solvent capable of dissolving the polymer, and solidifying the liquid mixture to form the polymeric body.

SUMMARY OF THE INVENTION

In general, the invention features an improved method of making such a body, in which the liquid mixture further includes water; solidification is carried out by cooling the mixture to a temperature sufficiently low to cause the water in the mixture to freeze, thereby creating channels in the body for the release of the active substance therefrom; and removing the organic solvent and the water from the body.

In preferred embodiments, the organic solvent is immiscible with water, so that the mixture is an emulsion; the removing of water and solvent is facilitated by subjecting the body to reduced pressure; the polymer is an ethylene-vinyl ester copolymer of the general formula:

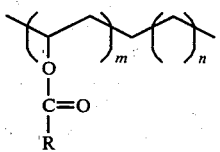

wherein R is hydrogen, lower alkyl of 1 to 7 carbons, or aryl, m is 10 to 40% by weight, and n is (100-m)% by weight; and the biologically active substance is an enzyme, a hormone, an enzyme inhibitor, an antigen, or a drug.

The new method provides improved drug release kinetics because of channel formation caused by freezing of the water. Adjustment of release rate to fit a given applicaion can be achieved by varying the water:-polymer ratio or the concentration of the active substance. Furthermore, because many active substances are available only as aqueous solutions or dispersions, the new method obviates complicated and potentially destructive (e.g., denaturing) procedures for isolating and purifying the active substance.

Additional advantages and features of the invention will be apparent from the following description of the preferred embodiments thereof, and from the claims.

DESCRIPTION OF THE PREFERRED EMBODIMENTS

We turn now to a description of the preferred embodiments, first briefly describing the drawings.

DRAWINGS

Figure 1:
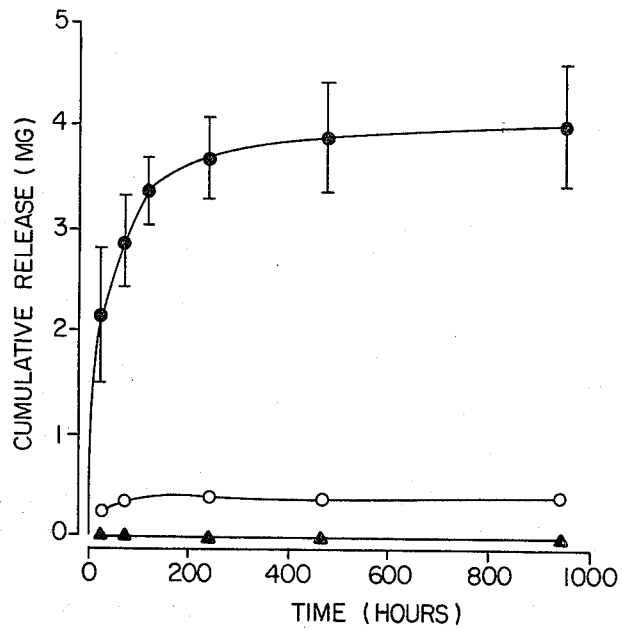

FIG. 1 is a graph of the relation between water:-polymer ratio and the release profile of bovine serum albumin (BSA) from polymeric bodies made according to the method of the invention; ▲——▲ = 2.0 ml 10% ethylene vinyl acetate copolymer (EVA) mixed with 0.1 ml 5% BSA; ○——○ = 2.0 ml 10% EVA mixed with 0.2 ml BSA; ●——● = 2.0 ml 10% EVA mixed with 0.3 ml 5% BSA.

Figure 2:
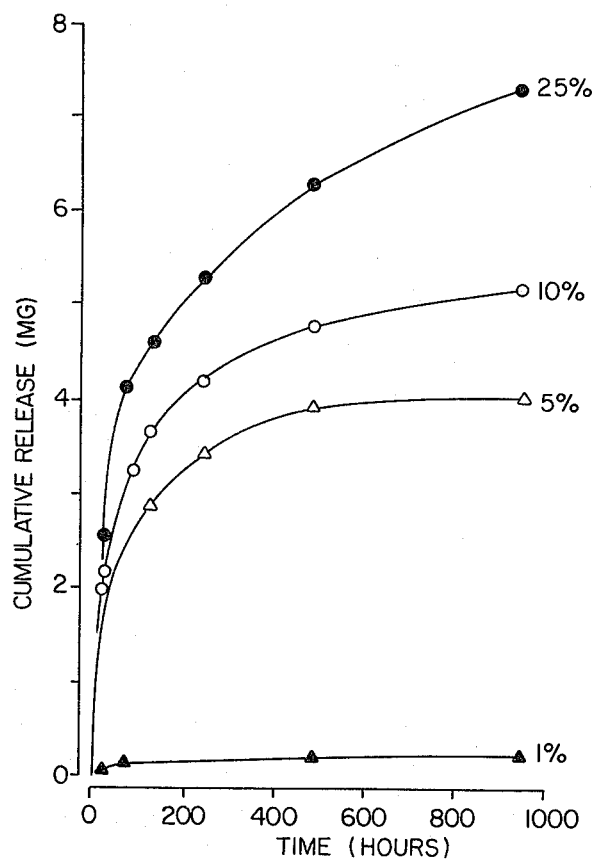

FIG. 2 is a graph of the relation between protein concentration and release profile in such bodies; ▲——▲ = 2.0 ml 10% EVA mixed with 0.3 ml 1% BSA; △——△ = 2.0 ml 10% EVA mixed with 0.3 ml 5% BSA; ○——○ = 2.0 ml 10% EVA mixed with 0.3 ml 10% BSA; ●——● = 2.0 ml 10% EVA mixed with 0.3 ml 25% BSA.

MANUFACTURE

EVA (available as ELVAX 40 from the DuPont Chemical Company, Wilmington, Del.), 40% vinyl acetate by weight, in pellet form, is washed ten times in distilled water, and then 50 times in absolute ethanol, and is then dissolved in methylene chloride to produce a 10% w/v solution. An aqueous protein solution (5% w/v) of type I calf intestine alkaline phosphatese is then prepared, and 0.3 ml of this solution is combined with 2.0 ml of EVA solution. The resultant casting mixture is shaken in a 3 ml scintillation vial, silicated with Prosil-28 (PCR Research Chemicals) for 60 sec. on a Vortex-Genie mixer at speed "10" to yield a uniform solution, which is quickly poured into a 2 cm×2 cm×0.5 cm glass mold which has been previously cooled by placing it on dry ice for 10 minutes. After 5.0 min., the frozen slab is removed by encircling the inside wall of the mold with a cold spatula tip and then prying the slab loose. The slab is transferred onto a cold wire screen in a freezer and kept at −20° C. for two days.

Water is then removed from the slab by lowering its temperature to −80° C. The slab is then lyophilized by placing it in a glass petri dish enclosed in a cardboard box, which is enclosed in a dessicator connected to a Vir-Tis Model 10-148 continuous MRBA lyophilizer. Lyophilizaton is carried out for three days at a pressure below 50 millitors; the lowered pressure increases the rate of water removal. The dried slab weighs 168±7 mg and is about 13 mm square and 1 mm thick.

The casting procedure described above is repeated, using, in place of 0.3 ml 5% alkaline phosphotase, the following aqueous solutions of biologically active, proteinaceous substances: 0.1 ml, 0.2 ml, and 0.3 ml 5% (w/v) bovine serum albumin (BSA); 0.3 ml of 1%, 10%, and 25% (w/v) BSA; 0.3 ml 5% (w/v) type II bovine pancreas alph-chymotrypsin; 0.3 ml 5% (w/v) porcine stomach mucosa pepsin.

Operation

The release of proteins from the slabs into 0.9 w/v saline is measured by placing each slab in a scintillation vial with 10 ml of saline and rotating the vials on a Thomas Rotating Apparatus set at speed 4. Each slab is periodically transferred to a new vial containing fresh saline. The released protein concentrations are determined spectrophotometrically by measuring absorbance at 220 μm.

FIG. 1 shows that in the case of BSA, increasing the water:polymer ratio increases the cumulative percentage of protein released over time. This is consistent with the observation that increasing the water:polymer ratio also produces a slab with a greater volume; the increased volume probably is a reflection of greater porosity and channel tortuosity resulting from the expansion of a greater amount of ice.

FIG. 2 shows that cumulative protein release increases with increased protein concentration in BSA slabs.

Other Embodiments

Other embodiments are within the following claims. For example, the active substance concentration and water:polymer ratio can be varied to obtain the release rate desired for a given application. The details of the method can also be varied. For example, drying need not be carried out under reduced pressure.

Any biologically active substance can be used, in conjunction with any biologically compatible, water-insoluble polymer and any organic solvent capable of dissolving the polymer. The active substance can be protein or it can be non-proteinaceous, it can be a macromolecule (M.W. over 1000 daltons) or a smaller molecule, and it can be soluble or insoluble in water. Examples of suitable active substances are insoluble in water. Examples of suitable active substances are interferon, anti-angiogenesis factors, antibodies, antigens, polysaccharides, growth factors, hormones, including insulin, glucagan, parathyroid, and pituatary hormones, calcitonin, vasopressin, renin, prolactin, growth hormones, thyroid stimulating hormone, corticotrophin, follicle stimulating hormone, luteinisinng hormone, and chorionic gonadatrophin; enzymes, including soybean trypsin inhibitor, lysozyme, catalase, tumor angiogenesis factor, cartilege factor, transfereses, hydrolases, lysases, isomerases, proteases, ligases, and oxidoreductases such as esterases, phosphatases, glycosidases, and peptidases; enzyme inhibitors such as leupeptin, antipain, chymostatin, and pepstatin; and drugs.

Suitable polymers include acyl substituted cellulose acetates and alkyl derivatives thereof; partially and completely hydrolyzed alkylene-vinyl acetate copolymers; unplasticized polyvinyl chloride; crosslinked homo- and co-polymers of polyvinyl acetate; crosslinked polyesters of acrylic and methacrylate; polyvinyl alkyl ethers; polyvinyl fluoride; silicone; polycarbonate; polyurethane; polyamide; polysulphones; styrene acrylonitrile copolymers; crosslinked poly(ethylene oxide); poly(alkylenes); poly(vinyl imidazole); poly(esters); poly(ethylene terephthalate); and chlorosulphonated polyolefins.

EVA, the most preferred polymer, is a member of a class of suitable polymers of the general formula

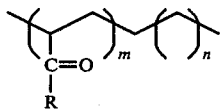

wherein R is hydrogen, lower alkyl of 1 to 7 carbons, or aryl, and m is (10 to 40)% by weight and n is (100-m)% by weight. Typical alkyl groups include ethyl, propyl, isopropyl, tert-butyl, pentyl, and hexyl. Suitable ethylene-vinyl ester copolymers are the acetates, include ethylene-vinyl acetate, ethylene-vinyl methylacetate, ethylene-vinyl ethylacetate, ethylene-vinyl propylacetate, and the like.

Polymer bodies can be made, according to the method of the invention, in any desired shape. The shape will sometimes be determined by the body's location. Alternatively, the shape can be chosen to affect release kinetics. For example, zero order release kinetics (a release rate independent of active substance concentration) can be obtained by casting the body in the shape of a hemisphere which is sealed everywhere except in a depression on its flat surface, through which the active substance is released.

Polymer bodies made according to the method of the invention are implanted in animals, including humans, to provide controlled, prolonged release of the desired biologically active substance. Some medical applications of these polymer bodies are the prolonged release of insulin for the control of diabetes, immunizations (the active substance is an antigen), the delivery of informational macromolecules for assays for biological molecules such as tumor angiogenisis factor, and the prolonged treatment of a variety of medical disorders with the appropriate drugs.

We claim:

1. In a method of making a biologically compatible, implantable water-insoluble polymeric body for the controlled, prolonged release of a biologically active substance to a surrounding aqueous environment, said method comprising forming a liquid mixture containing said polymer, said active substance, and an organic solvent capable of dissolving said polymer, and solidifying said liquid mixture to form said polymeric body, the improvement wherein said liquid mixture further comprises water, and said organic solvent is immiscible with water, so that said mixture is an emulsion said solidification is carried out by cooling said liquid mixture to a temperature sufficiently low to cause the water in said mixture to freeze, thereby creating channels in said body for the release of said active substance therefrom, and said method further includes the steps of removing said organic solvent and said water from said body.

2. In the method of claim 1, the improvement wherein said removing of said solvent and water is facilitated by subjecting said body to reduced pressure.

3. In the method of claim 1, the improvement wherein said polymer is an ethylene-vinyl ester copolymer of the general formula:

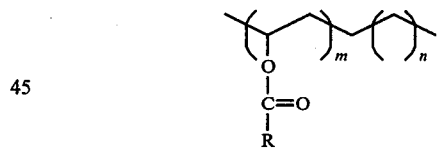

wherein R is hydrogen, lower alkyl of 1 to 7 carbons, or aryl, m is (10 to 40)% by weight and n is (100-m)% by weight.

4. In the method of claim 1, the improvement wherein said biologically active substance is an enzyme.

5. In the method of claim 1, the improvement wherein said biologically active substance is a hormone.

6. In the method of claim 1, the improvement wherein said biologically active substance is an enzyme inhibitor.

7. In the method of claim 1, the improvement wherein said biologically active substance is an antigen.

8. In the method of claim 1, the improvement wherein said biologically active substance is a drug.

9. The method of claim 1, the improvement wherein said body is in the shape of a hemisphere having a depression on its flat surface through which said active substance is released, said body being sealed everywhere except at said depression.

* * * * *